(12) United States Patent
Moeller et al.

(10) Patent No.: US 8,241,013 B2
(45) Date of Patent: Aug. 14, 2012

(54) SERIAL CAPILLARY PUMP

(75) Inventors: Mark W. Moeller, Kingston, MA (US); Daniel J. McCormick, Westford, MA (US); Joseph A. Luongo, Walpole, MA (US)

(73) Assignee: Waters Technologies Corporation, Milford, MA (US)

( * ) Notice: Subject to any disclaimer, the term of this patent is extended or adjusted under 35 U.S.C. 154(b) by 658 days.

(21) Appl. No.: 12/089,713

(22) PCT Filed: Oct. 24, 2006

(86) PCT No.: PCT/US2006/060206
§ 371 (c)(1),
(2), (4) Date: May 29, 2009

(87) PCT Pub. No.: WO2007/051113
PCT Pub. Date: May 3, 2007

(65) Prior Publication Data
US 2010/0024906 A1  Feb. 4, 2010

Related U.S. Application Data

(60) Provisional application No. 60/730,719, filed on Oct. 27, 2005.

(51) Int. Cl.
*F04B 49/00* (2006.01)
*F16K 5/10* (2006.01)
*F16K 11/087* (2006.01)

(52) U.S. Cl. .................... 417/286; 417/532; 137/625.41; 251/208

(58) Field of Classification Search ............. 137/624.41; 251/208; 417/286, 532
See application file for complete search history.

(56) References Cited

U.S. PATENT DOCUMENTS

| 3,193,148 A | 7/1965 | Anthon |
| 3,223,123 A | 12/1965 | Young |
| 3,584,977 A | 6/1971 | Coleman, II et al. |

(Continued)

FOREIGN PATENT DOCUMENTS

EP    0367099    5/1990

(Continued)

OTHER PUBLICATIONS

International Application No. PCT/US06/60206, Written Opinion of the International Searching Authority, Mailing Date: Oct. 1, 2007, 4 pages.

(Continued)

*Primary Examiner* — Karabi Guharay
*Assistant Examiner* — Michael Santonocito
(74) *Attorney, Agent, or Firm* — Jamie H. Rose

(57) ABSTRACT

Embodiments of the present invention are directed to devices and methods for propelling fluids that feature at least one first pump assembly having a primary pump, an accumulator pump, drive means, valve means and control means. The valve means moves between the first position and the second position as the accumulator pump and primary pump alternate between a loading movement and a pump movement. The control means is in signal communication with the accumulator pump, the primary pump and the valve means. The control means issues signal command to the accumulator pump to assume the loading movement and the pump movement and the primary pump to assume the loading movement and pump movement in coordination with the movement of the valve means such that fluids are propelled from the first outlet.

29 Claims, 9 Drawing Sheets

U.S. PATENT DOCUMENTS

| | | | |
|---|---|---|---|
| 3,851,795 A | 12/1974 | Anderson | |
| 4,068,528 A * | 1/1978 | Gundelfinger | 73/864.84 |
| 4,245,963 A | 1/1981 | Hutchins et al. | |
| 4,352,636 A | 10/1982 | Patterson et al. | |
| 4,599,049 A | 7/1986 | Gordon et al. | |
| 4,600,365 A | 7/1986 | Riggenmann | |
| 4,681,513 A | 7/1987 | Saito et al. | |
| 4,808,077 A | 2/1989 | Kan et al. | |
| 4,883,409 A | 11/1989 | Strohmeier et al. | |
| 4,913,624 A | 4/1990 | Seki et al. | |
| 4,915,591 A | 4/1990 | Funke | |
| 5,114,314 A | 5/1992 | Fujimoto | |
| 5,117,109 A | 5/1992 | Asakawa et al. | |
| 5,183,486 A | 2/1993 | Gatten et al. | |
| 5,572,919 A | 11/1996 | Ishizaki | |
| 5,637,208 A | 6/1997 | Dourdeville | |
| 5,653,876 A | 8/1997 | Funke | |
| 5,741,005 A | 4/1998 | Vaughan et al. | |
| 5,897,781 A | 4/1999 | Dourdeville | |
| 5,920,006 A | 7/1999 | Zelechonok | |
| 5,993,654 A | 11/1999 | Black | |
| 6,105,829 A | 8/2000 | Snodgrass et al. | |
| 6,228,153 B1 | 5/2001 | Saitoh | |
| 6,257,052 B1 | 7/2001 | Zelechonok | |
| 6,299,767 B1 | 10/2001 | Dourdeville | |
| 6,502,448 B1 | 1/2003 | Rapkin | |
| 2003/0098076 A1* | 5/2003 | Nichols | 137/625.46 |
| 2003/0143123 A1* | 7/2003 | Maeda | 422/100 |
| 2004/0014227 A1 | 1/2004 | Frederick et al. | |
| 2004/0082904 A1 | 4/2004 | Houde et al. | |
| 2004/0151594 A1 | 8/2004 | Allington et al. | |
| 2005/0019187 A1 | 1/2005 | Whitworth et al. | |
| 2005/0132881 A1 | 6/2005 | Baksh et al. | |
| 2005/0194298 A1 | 9/2005 | Usowicz et al. | |

FOREIGN PATENT DOCUMENTS

| | | |
|---|---|---|
| JP | 62-157296 | 7/1987 |
| NL | 102910 | 5/1962 |

OTHER PUBLICATIONS

International Application No. PCT/US06/60206, International Preliminary Report on Patentability, Mailing Date: Apr. 29, 2008, 5 pages.

\* cited by examiner

SERIAL CAPILLARY PUMP

CROSS REFERENCE TO RELATED APPLICATIONS

This application claims benefit of U.S. Provisional Application No. 60/730,719, filed Oct. 27, 2005, the content of which is incorporated herein by reference.

STATEMENT REGARDING FEDERAL SPONSORSHIP

The present invention was not made or developed with Federal sponsorship.

FIELD OF INVENTION

This invention relates to pumps and pumping systems. Embodiments of the present invention have particular utility in pumps used for chromatography.

BACKGROUND OF THE INVENTION

Embodiments of the present invention are directed to pumps, pumping systems, valves used to operate such pumps and pumping systems and methods of using such pumps and pumping systems. The pumps and pumping systems of the present invention have particular utility in applications in which a constant flow is desired.

Chromatography is the separation of mixtures of compounds in solution as the solution passes through or over an immobile non-miscible or stationary phase. The compounds of the mixture separate as a result of the individual and different affinity each compound has for the stationary or immiscible phase. The compound held in solution is referred to as the analyte. The material in which the compound is dissolved is known as the solute.

High performance liquid chromatography (HPLC) processes use one or more pumps to propel a liquid solution through a stationary phase. Gas chromatography methods use pressurized or pumped gases to propel a gas solution through or against a stationary phase. Super-critical gas chromatography employs gases at temperatures and pressures such the gases have liquid-like salvation properties and gas like permeability properties.

Many chromatographic processes employ a stationary phase of packed particles or a porous monolithic material, contained in a column or cartridge, through which a solution is passed. Capillary chromatography uses a fine tube, or capillary, either packed with particles, or using the walls of the capillary, to effect separations.

Chromatography pumps normally operate at pressures of up to 5,000 to 6000 psi and, even more preferably, up to 15,000 psi. Compounds are frequently identified by a characteristic time of retention. The retention time is the period of time in which the material is retained in the stationary phase after entering. Compounds elute or leave the stationary phase either due to time or change in the composition of the fluids flowing through the stationary phase. It is common to change the composition of the solution over time to release compounds from the stationary phase.

Some of the solutions routinely used in performing chromatography are difficult to pump precisely due to the change of volume of the liquid as it is compressed and undergoes changes in temperature. Some of the solutions are corrosive, leave residue, dissolve mechanical parts of the pump, or become gaseous when subjected to changes in pressure.

It is desirable to pump the liquids and gases used in chromatographic process at a constant flow rate. However, if the composition of the solution is changing over time, the difficult task of maintaining constant flow to a column, cartridge or capillary becomes even more complex.

Thus, there is a need for pumps that can propel fluids with precise control of the flow rate, with few pressure perturbations and with a minimum of moving mechanical parts in contact with fluids.

SUMMARY OF THE INVENTION

Embodiments of the present invention are directed to devices and methods for propelling fluids. One embodiment of the present invention directed to a device comprises at least one first pump assembly having a primary pump, an accumulator pump, drive means, valve means and control means.

The primary pump has a primary housing, a primary piston, and drive means. The primary housing has a primary opening and primary chamber. The primary opening is in fluid communication with the primary chamber. And, the primary piston is movable within the primary chamber to move fluids through the primary opening. The drive means is mechanically linked to at least one of the primary piston and primary chamber. The drive means powers the primary piston in a loading movement in which the primary piston withdraws from the primary chamber and a pump movement in which the primary piston enters the primary chamber.

The accumulator pump has an accumulator housing, accumulator piston and accumulator drive means. The accumulator housing has an accumulator opening and an accumulator chamber. The accumulator opening is in fluid communication with said accumulator chamber. And, the accumulator piston is movable within said accumulator chamber to move fluids through said accumulator opening. The accumulator drive means is mechanically linked to at least one of the accumulator piston and accumulator chamber. The drive means powers the accumulator piston in a loading movement in which the accumulator piston is withdrawn from the accumulator chamber and a pump movement in which the accumulator piston enters the accumulator chamber.

The valve means is in fluid communication with the accumulator opening and the primary opening. The valve means has a first outlet and a first inlet, and at least a first position and a second position. The first inlet is for receiving fluid and the first outlet is for discharging fluid. In the first position the accumulator opening and the first outlet are in fluid communication, and the primary opening is in fluid communication with the first inlet. Upon said accumulator pump assuming the pump movement, the first outlet discharges fluid. And, upon the primary opening assuming the loading movement, the primary chamber is filled with fluid. In the second position, the primary pump opening, accumulator pump opening and first outlet are in fluid communication. And, upon the primary pump assuming the pumping movement and the accumulator pump assuming the loading movement, the accumulator chamber fills with fluid and the first outlet discharges fluid. The valve means moves between the first position and the second position as the accumulator pump and primary pump alternate between a loading movement and a pump movement.

The control means is in signal communication with the accumulator pump, the primary pump and the valve means. The control means issues signal command to the accumulator pump to assume the loading movement and the pump movement and the primary pump to assume the loading movement and pump movement in coordination with the movement of the valve means such that fluids are propelled from the first outlet.

As used herein, the terms "primary drive means" and "accumulator drive means" refer to gears, transmissions, belts, cams and motors used to power and move, relative to each other, pistons and pump chambers. As used herein, the term "valve means" refers to a valve with fittings and conduits to make the recited connections. The term further comprises valve drive means, which for the purpose of clarity is not expressly recited above. Such drive means comprise, by way of example, without limitation, solenoids, gears, transmissions, belts and motors to effect movement of surfaces within the valve that direct the flow of fluid. The term is used to include rotary valves and, in particular, multi-port rotary valves, and specifically exclude check valves and powered check valves which do not have the required number of ports and openings to operate in the context of the present invention. The term "control means" is used to denote a central processing unit (CPU), embedded or stand-alone computer, and software and firmware for programming such control means in the recited manner.

Preferably, the device has at least one first pressure sensor in fluid communication with the primary pump. The first pressure sensor produces at least one first pressure signal indicative of the pressure in the primary pump to allow control means to command the valve means to assume the second position. Preferably, the device has at least one second pressure sensor in fluid communication with the accumulator pump. The second pressure sensor produces at least one second pressure signal indicative of the pressure in the accumulator pump to allow the control means to command the valve means to assume the second position. And, where there is a first pressure sensor and a second pressure sensor, the control means commands the valve means to assume the second position, with the primary pump in fluid communication with said accumulator pump, upon the first pressure signal corresponding to the second pressure signal. As used herein, the term "corresponding" refers to equal or approximately equal.

Preferably, the control means commands the valve means to assume the first position upon the accumulator pump completing a loading movement with the accumulator assuming a pump movement and said primary assuming a loading movement. Thus, the device presents a serially pumped pump in which fluid flows from a primary pump to an accumulator pump.

Preferably, the valve means has a first intermediate position. The first intermediate position is in between the first position and the second position, and in the first intermediate position the accumulator chamber is in communication with said outlet and said primary chamber is closed. The closed primary chamber allows the primary drive means to power the primary piston to bring the pressure of the primary chamber to a pressure corresponding to the pressure of the accumulator pump as measured by the first pressure sensor and the second pressure sensor. Matching the pressure of the accumulator chamber and the primary chamber minimizes pressure perturbations.

In addition, the intermediate position is preferably used to check for system failure. System failure can be performed by powering the primary pump with the valve means in the intermediate position. The closed primary chamber becomes pressurized and the values of the first pressure sensor can be compared to anticipated control values, or the rate of decay of the pressure values compare to a control rate of decay. Failure to attain or maintain the pressure values or steeper decay rates are indicative of leaks.

Preferably, the valve means has a second intermediate position. In the second intermediate position the accumulator opening is closed. And, preferably, the control means directs said valve means to assume the second intermediate position and the accumulator pump to assume a pump movement to check for system failure by comparing the pressure signal from the accumulator pressure sensor to predetermined minimum values and a values determined by a pressure value decay rate. Failure to attain or maintain anticipated pressure values or decay rates steeper than control values are indicative of leaks.

Preferably, the control means is programmed to automatically check for system failure. This can be performed with each pump cycle with respect to the primary pump.

Preferably, the valve means has a second outlet and a third position. In the third position, the accumulator opening and the primary opening are in fluid communication with the second outlet to allow the accumulator pump and the primary pump to discharge fluid. Preferably, the second outlet is in communication with waste. The second outlet allows the device to vent or clear the accumulator chamber and the primary chamber. Preferably, control means commands the valve means to assume the third position and the accumulator pump and primary pump to assume a pump mode to discharge fluid to waste.

Preferably, the valve means has a fourth position. In the fourth position, the accumulator opening is in fluid communication with the second outlet and the primary opening is in fluid communication with the first inlet allowing the primary pump to fill. In the fourth position, the control means is capable of commanding the valve means to assume the third position and said accumulator pump and primary pump to assume a pump position to empty the primary chamber and accumulation chamber. The valve means is capable of alternating between the third and fourth positions as the accumulator pump and primary pump alternate between pump mode and loading mode to pump fluid to waste.

The devices of the present invention are preferably used in tandem in situations where the solutions being pump need to change composition. Thus, one embodiment of the present invention features a second pump assembly. The first pump assembly has valve means with said first inlet for being placed in fluid communication with a first fluid and the second pump assembly having a first inlet for being placed in fluid communication with a first fluid or a second fluid. The first pump assembly has a first outlet in fluid communication with a combined outlet and second pump assembly has a first outlet in communication with a combined outlet to allow fluid having different ratios of a first and second fluid to be formed. The control means for the second pump assembly is preferably shared with that of the first pump assembly. However, a second control means for the second pump assembly can be readily employed and a third control means to calculate the pumping rates of the first pump assembly and the second pump assembly to attain the desired ratios may also be employed. Changes the ratio of said first fluid and second fluid are created by changing the rate of the pumping mode of at least one primary or accumulator pump of the first pump assembly and second pump assembly.

Preferably, the valve means has a second inlet. The second inlet is capable of being placed in fluid communication with priming apparatus when the valve means is in said first position. A preferred priming apparatus is selected from syringes pumps and pressurized fluid sources.

A further embodiment of the present invention is directed to a valve for controlling a pump assembly having a primary pump, an accumulator pump. As previously described the primary pump has a primary opening, primary chamber and an a primary piston. The primary opening is in fluid communication with the primary chamber. And, the primary piston is movable within the primary chamber to move fluids through the primary opening. The primary pump has a loading movement and a pump movement. The accumulator pump has an accumulator opening, accumulator chamber and an accumulator piston. The accumulator opening is in fluid communication with the accumulator chamber. And, the accumulator piston is movable within said accumulator chamber to move fluids through the accumulator opening. The accumulator pump has a loading movement and a pump movement.

The valve has a valve housing, a rotor means, and positioning means. The housing has an accumulator port, a primary port, a first inlet port, a first outlet port, first stator surface, and a second surface. The accumulator port is for placement in fluid communication with the accumulator opening and the primary port is for placement in fluid communication with the primary opening. The first inlet port is for placement in communication with the first inlet and the first outlet port is for placement in communication with the first outlet. The first stator surface is in sealing contact with a first rotor surface of the rotor means. The first stator surface has a first accumulator stator opening in fluid communication with the accumulator port, a first primary stator opening in fluid communication with the primary port, a first inlet stator opening in fluid communication to the first inlet port, and a first outlet stator opening in fluid communication with the first housing outlet port. The second surface is to press a the rotor means against the first stator surface.

The rotor means has a body with a first rotor surface, a second rotor surface, an axis of rotation and rotor passage means. The first rotor surface is in sealing contact with the first stator surface. The rotor passage means is in selectable communication with the accumulator stator opening, the primary stator opening, the inlet stator opening, and the outlet stator opening. The rotor means is coupled to positioning means for rotation about an axis of rotation to assume a first position and a second position. In the first position, the accumulator opening and the first outlet are in fluid communication and the primary opening is in fluid communication with the first inlet. And, in the second position, the primary pump opening, accumulator pump opening and first outlet are in fluid communication.

The positioning means is coupled to the rotor means to power the rotor means to one of the first position and second position to allow the valve to direct fluids in and out of the accumulator chamber and primary chamber in response to pumping and loading movements.

As used herein, the term "passage means" refers to tunnels, conduits, tubing, pipes, channels about surfaces and drilled passages. The term "positioning means" refers to stepper motors, solenoids, electric motors linked with position sensors and the like. It is common to have the stepper motor coupled to the rotor means through gearing.

Preferably, the housing further comprises a stator body and a first housing surface, wherein the first stator surface is integral to the stator body. The stator body has a second stator surface, which second stator surface is received in sealing relationship to the first housing surface. The first housing surface has an accumulator housing opening in fluid communication with said accumulator port, a primary housing opening in fluid communication with said primary port, an inlet housing opening in fluid communication to said first inlet port, and a outlet housing opening in fluid communication with said first housing outlet port. The stator second surface has a second accumulator stator opening in fluid communication with the first accumulator stator opening, a second primary stator opening in fluid communication with the first primary stator opening, a second inlet stator opening in fluid communication with the first inlet stator opening, and a second outlet stator opening in fluid communication with the first stator outlet.

Preferably, the first accumulator stator opening, the first primary stator opening, the first inlet stator opening, and the first stator outlet are arranged about a common radius defined by the rotation of the rotor means with respect to the stator body. And, preferably, the first accumulator opening has a radial channel section extending from said common radius to the axis of rotation on the first stator surface.

Preferably, the rotor means has a first rotor channel extending from the common radius to the axis of rotation on the first rotor surface to cooperate with the radial channel section. And, preferably, the rotor has a second rotor passage on the first rotor surface. The second rotor passage extends axially about the common axis to bring the first accumulator stator opening in fluid communication with the first primary stator opening in the first position.

Preferably, the housing has a second outlet and the rotor means has a third rotor channel on the first rotor surface. The third rotor passage extends axially about the common axis to bring the first accumulator stator opening in fluid communication with the first primary opening as the rotor means is in fluid communication with the second outlet to allow the primary pump and accumulator pump assume a loading and pumping movement with respect to said second outlet.

Preferably, the stator body has a second stator outlet in fluid communication with the second outlet. The second stator outlet has a third stator channel extending axially about the common axis a distance permitting the rotor means to maintain fluid communication as the primary pump and accumulator pump assume a loading and pumping movement.

Preferably, the housing has a second inlet and the stator body has a second stator inlet opening in fluid communication with the second inlet. The second stator inlet opening has a passage to the first inlet opening to allow the second inlet to receive priming fluids.

A embodiment of the present invention is directed to a method for propelling fluids. The method comprises the step of providing at least one first pump assembly having a primary pump, an accumulator pump, valve means, and control means. And, the method comprises the step of operating the one pump assembly to propel fluids as control means commands said valve means to assume a first position and a second position and commands said primary pump and accumulator pump to alternate between a loading movement and a pump movement.

Thus, embodiments of the present invention are directed to pumps capable of pumping the liquids and gases used in chromatographic processes at a constant flow rate with minimal pressure perturbations. Embodiments featuring tandem pump assemblies are ideally suited to pump solutions changing in composition over time. The pump accomplishes these tasks with a minimum of moving mechanical parts in contact with fluids.

These and other features and advantage will be apparent to those skilled in the art upon reading the detailed description that follows and viewing the drawing.

DETAILED DESCRIPTION OF THE INVENTION

The present invention wilt be described in detail as a pump for use in chromatography with the understanding that the invention has utility and application wherever propelling fluids is desired. The pump will be described as a serial pump for capillary chromatography. However, the present discussion is directed to preferred embodiments and should not be perceived as limiting.

Figure 1:
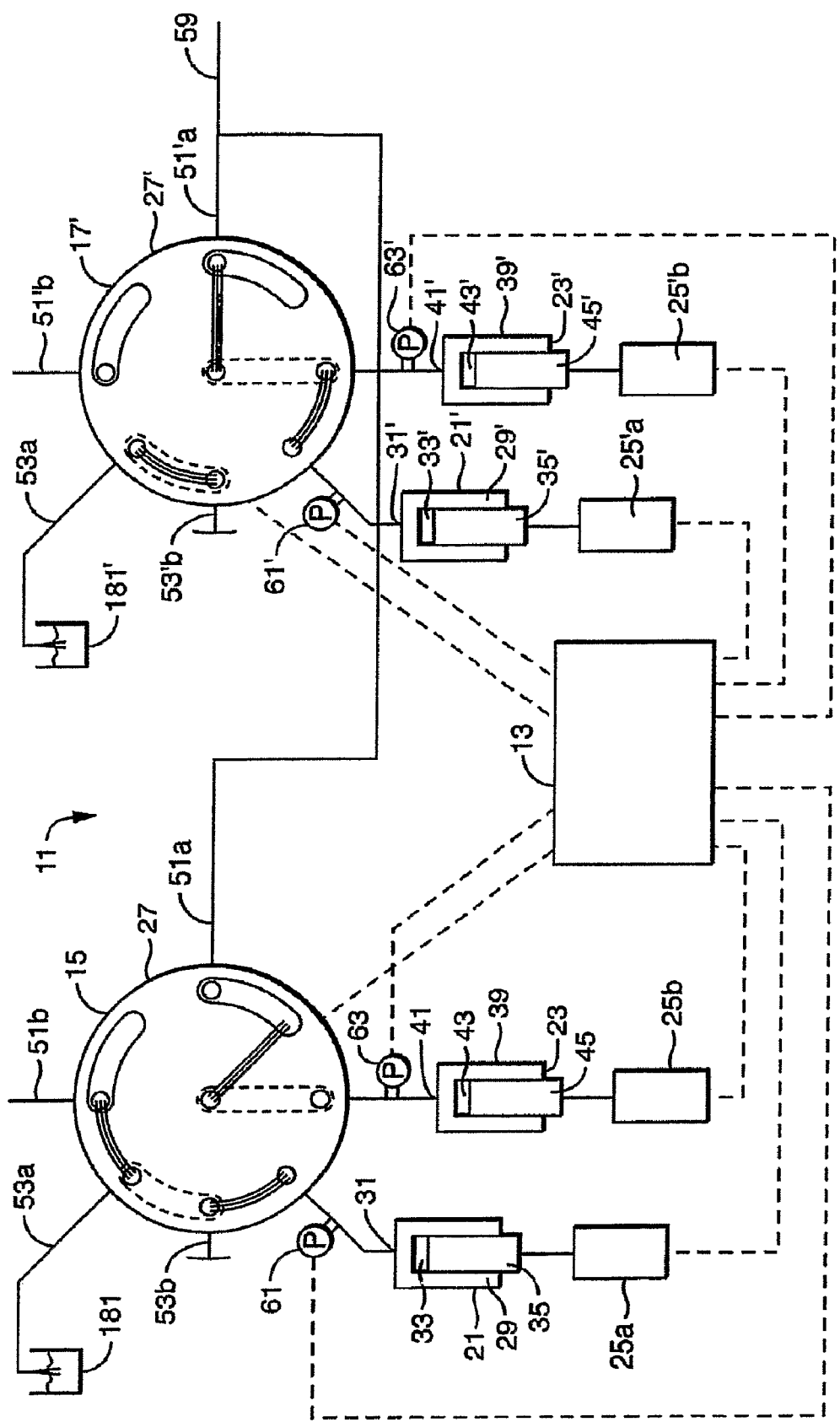
FIG. 1 illustrates in schematic form a device embodying features of the present invention.

Turning now to FIG. 1, one embodiment of the present invention, directed to a device for propelling fluid, a serial capillary scale pump, generally designated by the numeral 11, is depicted. The pump 11 has control means 13 and two pump assemblies, a first pump assembly 15 and a second pump assembly 17. First pump assembly 15 is substantially identical to second pump assembly 17. For purposes of clarity, this discussion will describe pump assembly 15 in detail with the understanding that the discussion, unless otherwise noted will apply equally to second pump assembly 17. And, although two pump assemblies 15 and 17 are depicted, those skilled in the art will readily recognize that more than two pump assemblies can be used in the context of the present invention. Or, the pump assemblies 15 and 17 can be used singularly and joined when desired.

First pump assembly 15 has a primary pump 21, an accumulator pump 23, drive means 25, and valve means 27.

The primary pump 21 has a primary housing 29 and a primary piston 35. Primary housing 29 has a primary opening 31 and primary chamber 33. The primary opening 21 is in fluid communication with the primary chamber 33. The primary piston 35 is movable within the primary chamber 33 to move fluids through the primary opening 31. Primary housing is machined of corrosion resistant metals, such as stainless steel, titanium or rigid plastics. Primary piston 35 is made of sapphire.

The drive means 25 has a primary drive 25a and an accumulator drive 25b. Primary drive 25a is mechanically linked to at least one of the primary piston 35 and primary housing 29. That is, the drive means 26a powers the relative movement of the primary piston 35 with respect to the primary chamber 33. The drive means 25a powers the primary piston 35 in a loading movement in which the primary piston 35 withdraws from the primary chamber 33 and a pump movement in which the primary piston 35 enters the primary chamber 33.

The drive means 25 is preferably stepper motors [not shown], electric motors with position sensing devices [not shown] known in the pump art, solenoid power devices [not shown], compressed air drives [not shown] and the like known in the art. These power devices are frequently coupled to the piston of pumps through gear drives, transmissions, belts, cams, screw drives and chains [not shown].

The accumulator pump 23 has an accumulator housing 39 and an accumulator piston 45. Accumulator housing 39 has an accumulator opening 41 and an accumulator chamber 43. The accumulator opening 41 is in fluid communication with the accumulator chamber 43. The accumulator piston 45 is movable within the accumulator chamber 43 to move fluids through said accumulator opening 41. The accumulator drive means 25b is mechanically linked to at least one of the accumulator piston 45 and accumulator housing 39. The accumulator drive means 25b powers the accumulator piston 45 with respect to accumulator housing 39 in a loading movement in which the accumulator piston 45 is withdrawn from the accumulator chamber 43 and a pump movement in which the accumulator piston 45 enters the accumulator chamber 43.

Valve means 27 comprises a valve with passages, fittings and conduits to make the recited connections. Such fittings and conduits are well known in the art. Conduits are normally tubing, capillaries and the like made of stainless steel. Fittings and conduits are available from numerous vendors. In the alternative, the accumulator housing 39 and primary housing 29 incorporate valve means 27.

Valve means 27 further comprises valve drive means, which for the purpose of clarity is not depicted in the figures. Such drive means are, indeed, well known in the art, and available from numerous vendors. The drive means comprise, by way of example, without limitation cams, solenoids, gears, transmissions, belts and motors, and in particular, stepper motors, to effect movement of surfaces within the valve that direct the flow of fluid. Stepper motors are available from PACIFIC SCIENTIFIC, (Rockford, Ill., USA) ORIENTAL MOTORS, (Torrence, Calif., USA).

Valve means 27 of the present invention comprise rotary valves and, in particular, multi-port rotary valves, and specifically exclude check valves and powered check valves which do not have the required number of ports and openings to operate in the context of the present invention. General purpose rotary multi-port valves are available from several vendors, including VALCO, (Houston, Tex., USA) and RHEODYNE (Rohnert Park, Calif., USA). A preferred rotary multi-port valve of the present invention will be discussed later in this paper.

The valve means 27 is in fluid communication with the accumulator opening 41 and the primary opening 31. The valve means 27 has a first outlet 51 and a first inlet 53. The first inlet 53a is for receiving fluid and the first outlet 51a is for discharging fluid. As depicted, valve means 27 has a second inlet 53a and a second inlet 51b. The second inlet 53a is associated with priming and the second outlet 51b is associated with waste and venting.

The valve means 27 has at least a first position and a second position. In the first position, represented by pump 15 of FIG. 1, the accumulator opening 41 and the first outlet 51a are in fluid communication, and the primary opening 31 is in fluid communication with the first inlet 53a. Passages are illustrated by solid lines and dotted lines. Ports and openings are represented by dark circles. Upon said accumulator pump 23 assuming a pump movement, the first outlet 51a discharges fluid. A pump movement is accumulator piston 45 entering the accumulator chamber 43. And, upon the primary pump 21 assuming a loading movement, the primary chamber 33 is filled with fluid. A loading movement is primary piston 35 withdrawing from the primary chamber 33.

The second position is represented by second pump 17 of FIG. 1. Features of the second pump 17 carry identical numeric identifiers with the prime mark. In the second position, the primary pump opening 31', accumulator pump opening 41' and first outlet 51a' are in fluid communication. And, upon the primary pump 21' assuming a pumping movement and the accumulator pump 23' assuming the loading movement, the accumulator chamber 43' fills with fluid and the first outlet 51a' discharges fluid.

The primary piston 35' operates at a speed to fill the accumulator chamber 43' being vacated by accumulator piston 45' and maintain a desire flow rate at the first outlet 51'. The valve means 27 of the first pump 15 and the valve means 27' of the second pump 17 move between the first position and the second position as the respective accumulator pumps 23 and 23' and primary pumps 21 and 21' alternate between a loading movement and a pump movement.

The first outlet 51a of first pump 15 is in fluid communication with the first outlet 51a' of the second pump 17 to form a combined outlet 59. As depicted, first inlet 53a of the first pump 15 is in fluid communication with a first solvent 63 and first inlet 53a' of the second pump is in fluid communication with a second solvent 65. The composition and the flow rate of the solutions discharged from the combined outlet 59 are determined by the respective flow rates of the first pump 15 and the second pump 17. For example, without limitation, in the event a constant flow rate was desired with a change of composition of the discharged solution, one of the first pump 15 and second pump 17 would be operated at a slower rate and remaining first pump 15 or second pump 17 would be operated at an increased rate.

The control means 13 is depicted in block form. Turning to first pump 15, the control means 13 is in signal communication with the accumulator pump 23, the primary pump 21 and the valve means 27. If a second pump 17 is desired, control means 13 may be shared with first pump 15 or a separate control means [not shown] used.

The control means is a central processing unit (CPU), embedded or stand-alone computer, and software and firmware for programming such control means in the recited manner. Computers and CPUs are available from numerous vendors. For example, CPUs and associated computer motherboards are sold by MOTOROLA (Shaumburg, Ill. USA), INTEL CORPORATION, (Santa Clara, Calif., USA) and AMD Corporation (Sunnyvale, Calif. USA). Stand-alone computers are available from venders such as Apple Corporation (Cupertino, Calif., USA) and Dell Corporation (Round Rock, Tex. USA).

Software developers skilled in the art routinely develop code for the control of valves and stepper motors which comprise the various drive means of the present invention. The manufactures of stepper motors and valves will provide the purchaser with control files and codes which the motor or valve recognize and the developers use such codes to program the CPU.

As used herein, the "signal communication" means electronically connected, or connected by way of optical or radio controls in the manner of wireless computer networks. The control means 13 issues signal commands to the accumulator pumps 23 and 23' of the first pump 15 and second pump 17 to assume the loading movement and the pump movement and the primary pumps 21 and 21' of the first pump 15 and second pump 17 to assume the loading movement and pump movement in coordination with the movement of the valve means 27 and 27' of the first pump 15 and second pump 17 such that fluids are propelled from the first outlet 51 and 51' and combined outlet 59.

Turning again to first pump 15, the device 11 has at least one first pressure sensor 61 in fluid communication with the primary pump 21 and signal communication with control means 13. The first pressure sensor 61 produces at least one first pressure signal indicative of the pressure in the primary pump 21 to allow control means 13 to command the valve means 27 to assume the second position. As depicted, the device 11 has at least one second pressure sensor 63 in fluid communication with the accumulator pump 23 and in signal communication with control means 13. The second pressure sensor 63 produces at least one second pressure signal indicative of the pressure in the accumulator pump 23 to allow the control means 13 to command the valve means 27 to assume the second position.

As depicted, the first pressure sensor 61 and a second pressure sensor 63, send signal indicative of the pressure in the accumulator pump 23 and primary pump 21. The control means 13 commands the valve means 27 to assume the second position, with the primary pump 21 in fluid communication with the accumulator pump 23, upon the first pressure signal corresponding to the second pressure signal. As used herein, the term "corresponding" refers to equal or approximately equal. Preferably, the control means 13 anticipates, based on the pressure signals, the time when the signals will correspond, to reduce pressure perturbations at the first outlet 51 caused by reaction times.

In summary, the control means 13 commands the valve means 27 to assume the first position upon the accumulator pump 23 completing a loading movement with the accumulator piston 45 assuming a pump movement and the primary piston 35 of primary pump 21 assuming a loading movement. Thus, the device presents a serially plumbed pump in which fluid flows from a primary pump 21 to an accumulator pump 23 to an outlet 51.

Figure 2A:
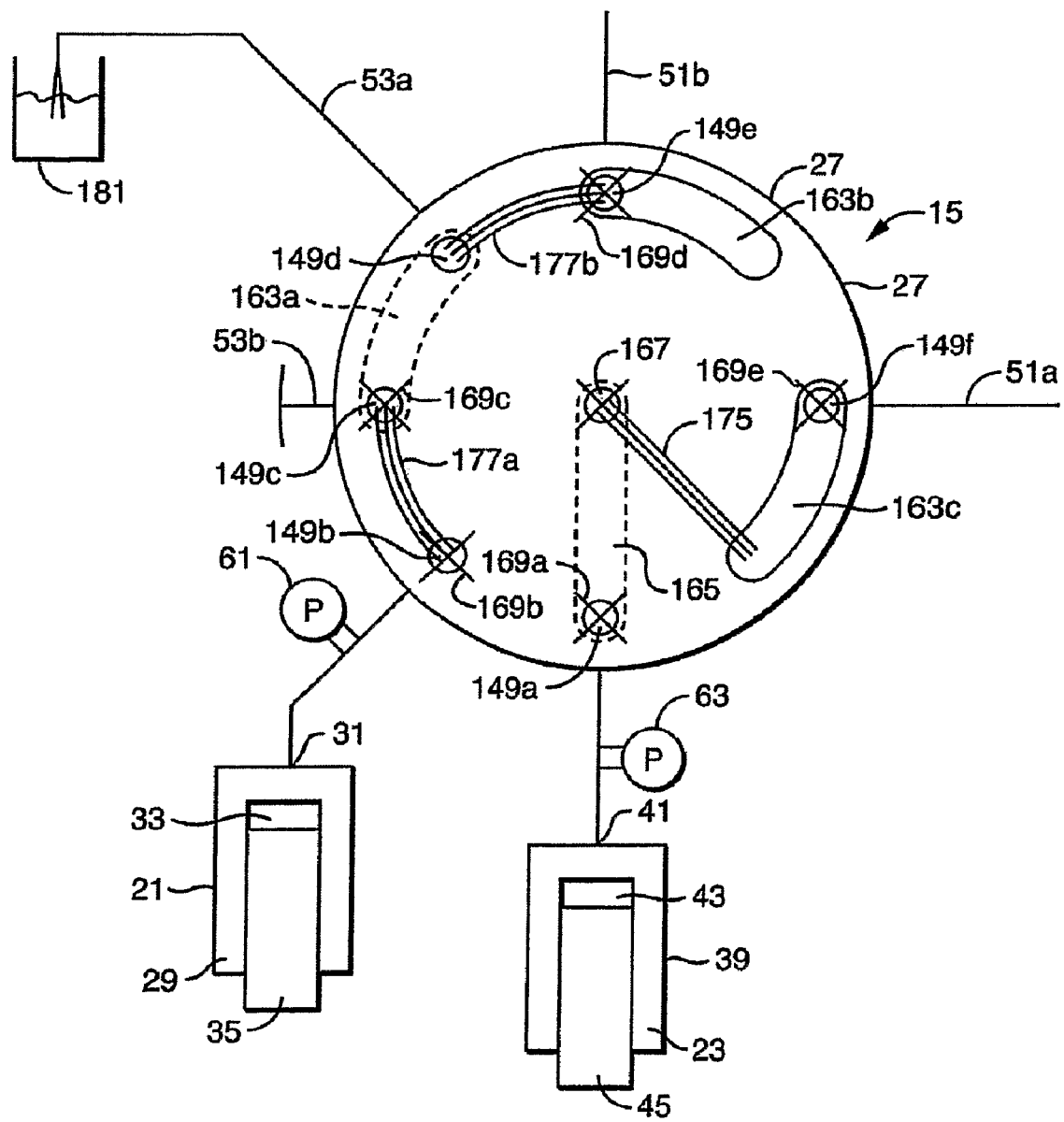
FIGS. 2A, 2B, 2C, 2D, 2E, and 2F depict the different positions of the valve means.

Turning now to FIG. 2A, first pump 15 is illustrated apart from second pump 17. The valve means 27 is depicted, highlighted in an enlarged perspective, in the first position in which the accumulator opening 41 is in communication with the first outlet 51a. And, the primary opening 31 is in fluid communication with the first inlet 53a. The valve means 27 of FIG. 2A-2G is a eight port valve of which only six ports are active and two are vacant and plugged or the housing is not plumbed for such ports, as will be described later.

Those skilled in the art will recognize that the present discussion regarding an eight port valve applies equally to valves having different numbers of ports. Embodiments of the present invention can be readily made with valves with greater or lesser numbers of ports. With respect to valves with greater numbers of ports, additional features can be performed by the device 11 due to greater flexibility in plumbing alternatives. However, valves with as few as three ports can used in embodiments of the present invention.

Figure 3:
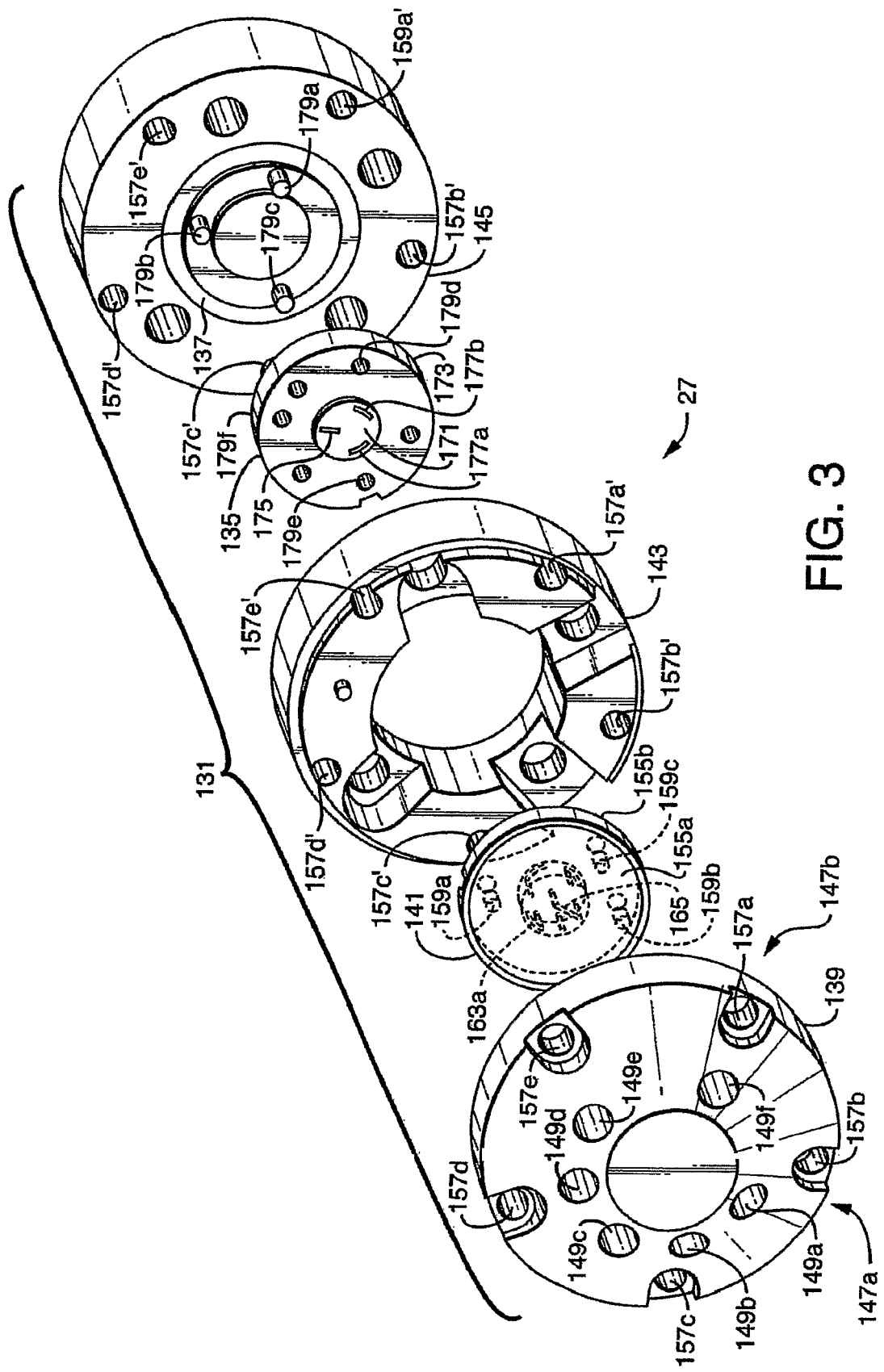
FIG. 3 depicts a valve means embodying features of the present invention.

Turning now to FIG. 3, a valve 127 is depicted in an expanded perspective. Valve 127 has the following major elements: a housing assembly 131, rotor 135 and shaft 137. The housing 131 has a port plate 139, a stator disc 141, middle plate 143 and a black plate 145. Port plate 139 has a front face 147a and a back face 147b. The port plate 139, middle plate 143 and back plate 145 are metal or plastic and, preferably, stainless steel.

For a capillary scale pump operating at pressures of 4-5, 000 pounds per square inch (PSI) and flow rates of approximately 0 to 1 milliliter (ml) per minute, the port plate 139, middle plate 143 and back plate 145 would be approximately one and a half to two inches in diameter. Each would be approximately three quarters to one inch in thickness. The stator disc 141 and the rotor 135 are approximately one half to three quarters of an inch in diameter and approximately one eighth of an inch in thickness.

The front face 147a is depicted with ports 149a, 149b, 149c, 149d, 149e and 149f arranged about a common axis defined by the rotation of rotor 135 and shaft 139. Ports 149a, 149b, 149c, 149d, 149e and 149f for receiving fitting and conduits [not shown] to place the valve 127 in communication with the primary pump 21, accumulator pump 23, first outlet 51 and first inlet 53 and others that will be described. For example, port 149a receives fitting and conduits in fluid communication with accumulator opening 41, port 149b receives fitting and conduits in fluid communication with primary opening 31, port 149c receives fittings and conduits in fluid communication with a second inlet 53b to be described in greater detail later, port 149d receives fittings and conduits in fluid communication with a first inlet 53a, port 149e receives fittings and conduits in fluid communication with a second outlet 51b to be described in greater detail later, and port 149f receives fittings and conduits in fluid communication with first outlet 51a.

Figure 4:
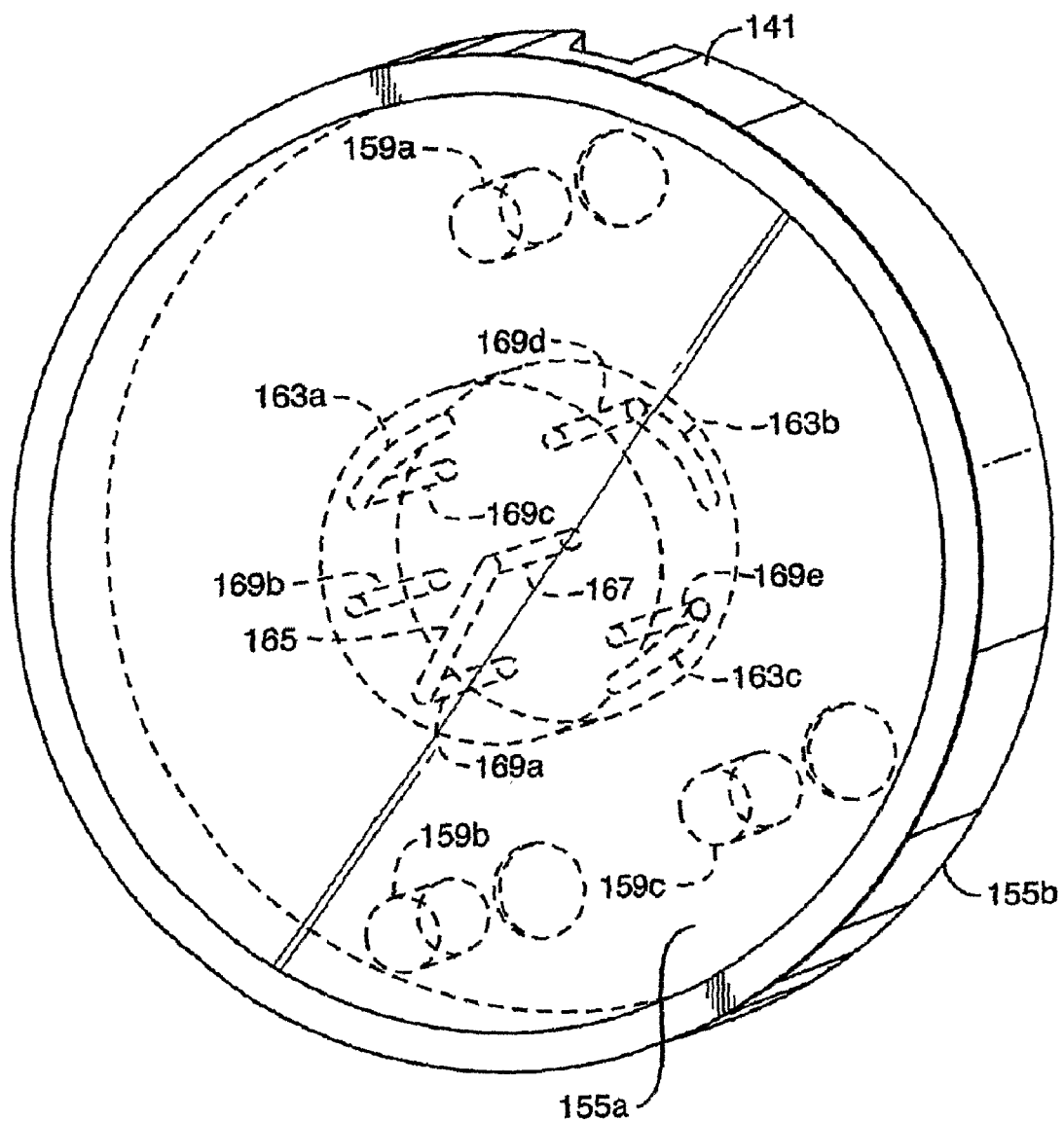
FIG. 4 depicts a stator disc embodying features of the present invention.

The port plate 139 has passages [not shown] from ports 149a, 149b, 149c, 149d, 149e and 149f to the back face 147b. These passages, for a capillary scale pump, are six to ten thousands of an inch in diameter. Back face 147b may act as a stator face or, preferably, housing assembly has a stator disc 141 as depicted. Stator disc 141 facilitates placing various ports 149a-f in fluid communication and permits wear surfaces to be replaced. As best seen in FIG. 4, stator disc 141 has a housing face 155a and a rotor face 155b, on the opposite side. Stator disc 141 is a plastic or machinable metal. A preferred material is a polyaryletherketone, such as polyetheretherketone and modified derivatives such as polytetrafluoroethylene to facilitate machining and to impart desirable wear characteristics.

Returning now to FIG. 3, the housing face 155a is received in sealing relationship with back face 147b of port plate 139 by compression exerted by housing assembly 131 on the stator disc 141 and rotor 135. Compression is created by fasteners such bolts and screws [not shown] that extend through bolt openings 157a in port plate 139, bolt openings 157b in middle plate 143 and bolt openings 157c in back plate 145. Middle plate 143 maintains the alignment of the rotor 135 and stator disc 141. Stator disc 141 is keyed to port plate 139 by way of pins 159 a-c, best seen in FIGS. 3 and 4, and cooperating pin openings 161 a-c [not shown].

At least one of the back face 147 and housing face 155a has a first arc channel 163a bringing ports 149c and 149d in fluid communication. The first arc channel 163a is machined into the face as a groove. As depicted, referring now to FIG. 47 first arc channel 153 is machined into the back face 147b.

At least one of the back face 147 and housing face 155a has a first radial channel 165 bringing port 149a, associated with the accumulator pump 23, in communication with a center passage 167 in stator disc 141. First radial passage 165 is machined into the face as a groove. Center passage 167 cooperates with channels and passages on the rotor 135 which will be discussed later.

Stator disc 141 has a first through passage 169a associated with accumulator pump 23 and port 149a. Stator disc 141 has a second through passage 169b associated with the first outlet 51a and port 149b. Stator disc 141 has a third through passage 169c associated with second outlet 51b and port 149c. And, stator disc 141 has forth through passage 169d associated with the first inlet 53a and port 149d. And, finally, stator disc 141 has a fifth through passage 169e associated with a second inlet 53b which will be discussed in greater detail later.

Stator disc 141 has a second arc channel 163b on the rotor face 155b associated with through passage 169d and a third arc channel 163c on the rotor face 155b associated with through passage 169f. The second arc channel 163b and the third arc channel 163c allow the rotor 135 to stay in fluid communication with passage 169d and passage 169f for a prolonged period of rotation. Each of the arc channels 163b and 163c are machined into the rotor face 155b as grooves.

Rotor 135 has a disc shaped body with a first rotor surface 171, a second rotor surface 173. Rotor 135 has an axis of rotation with shaft 137 aligned with the stator disc 141. The first rotor surface 171 is received in sealed relationship abutting the rotor face 155b of stator disc 141 by compressive forces exerted by the housing assembly 131 as described with respect to the stator disc 141.

Turning now to FIGS. 2A and 3, first rotor surface 171 had a channel or radial rotor passage 175 that is in communication with the accumulator opening 41 via port 149a and first radial passage 169a of the stator disc 141. The radial rotor passage 175, depicted as triple lines, extends from the axis of the rotor 135 to the grouping of arc channels 163a-c and through passages 169a-e of the stator disc 141.

Figure 2B:
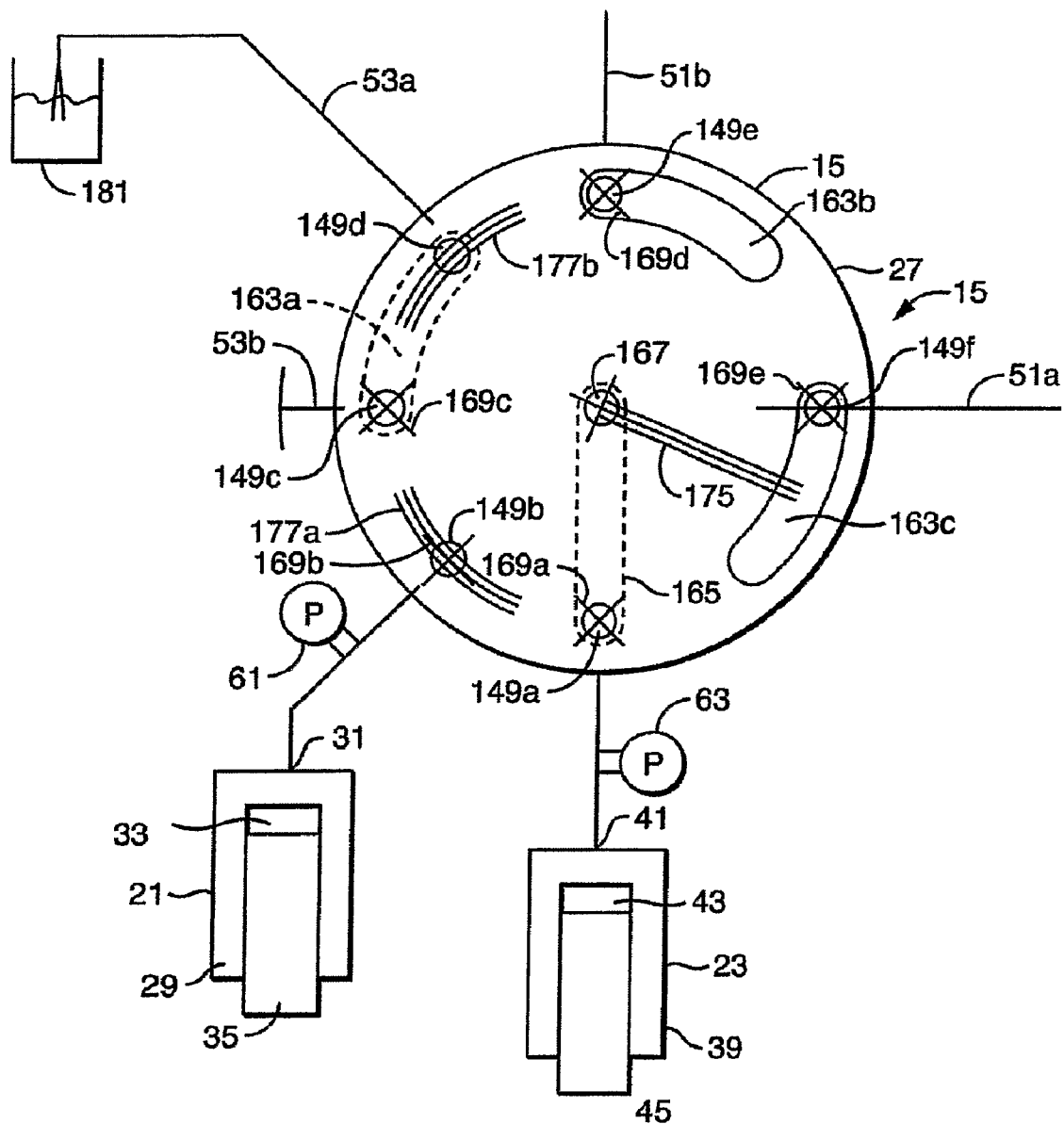
Figure 2C:
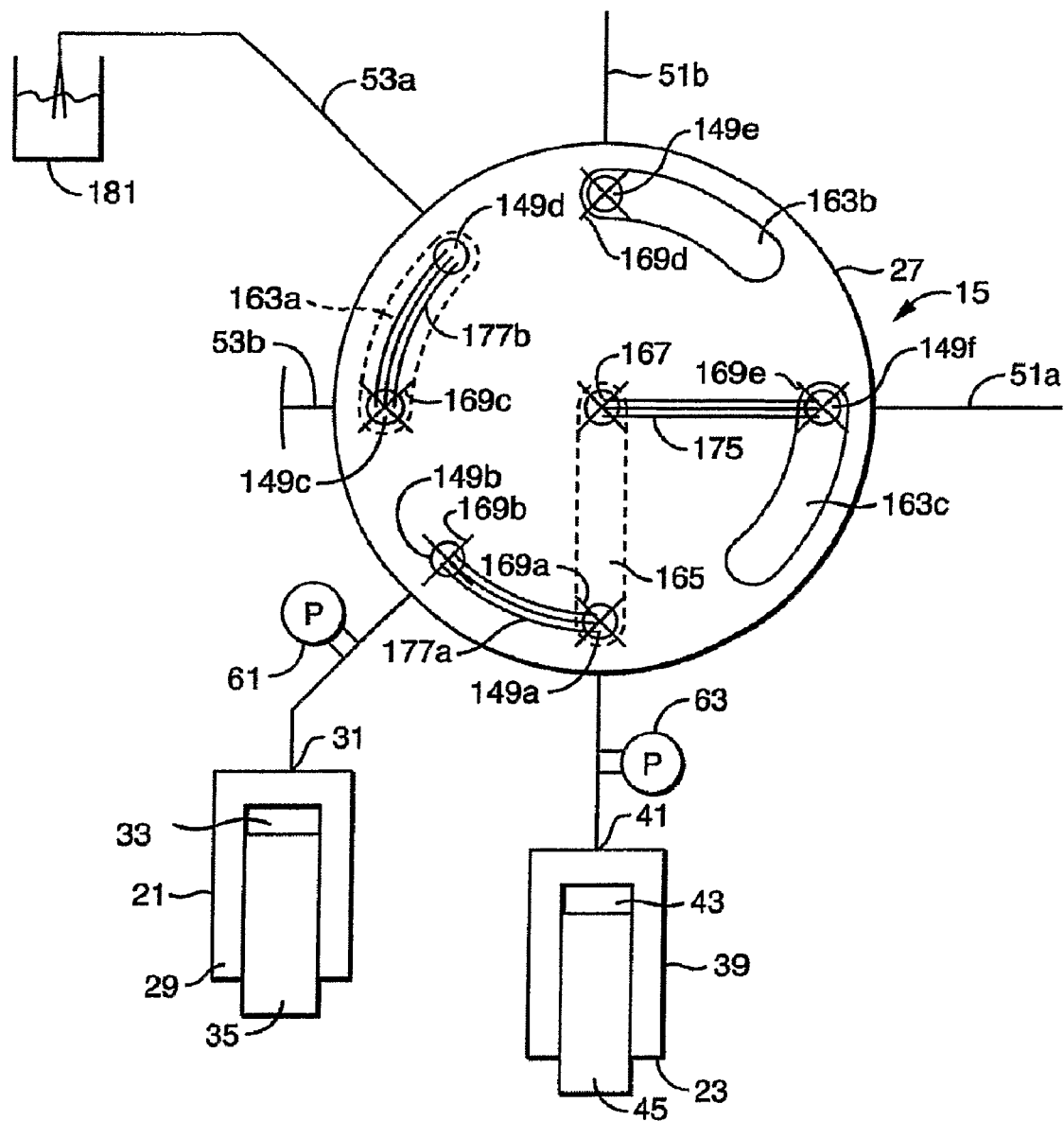
Figure 2D:
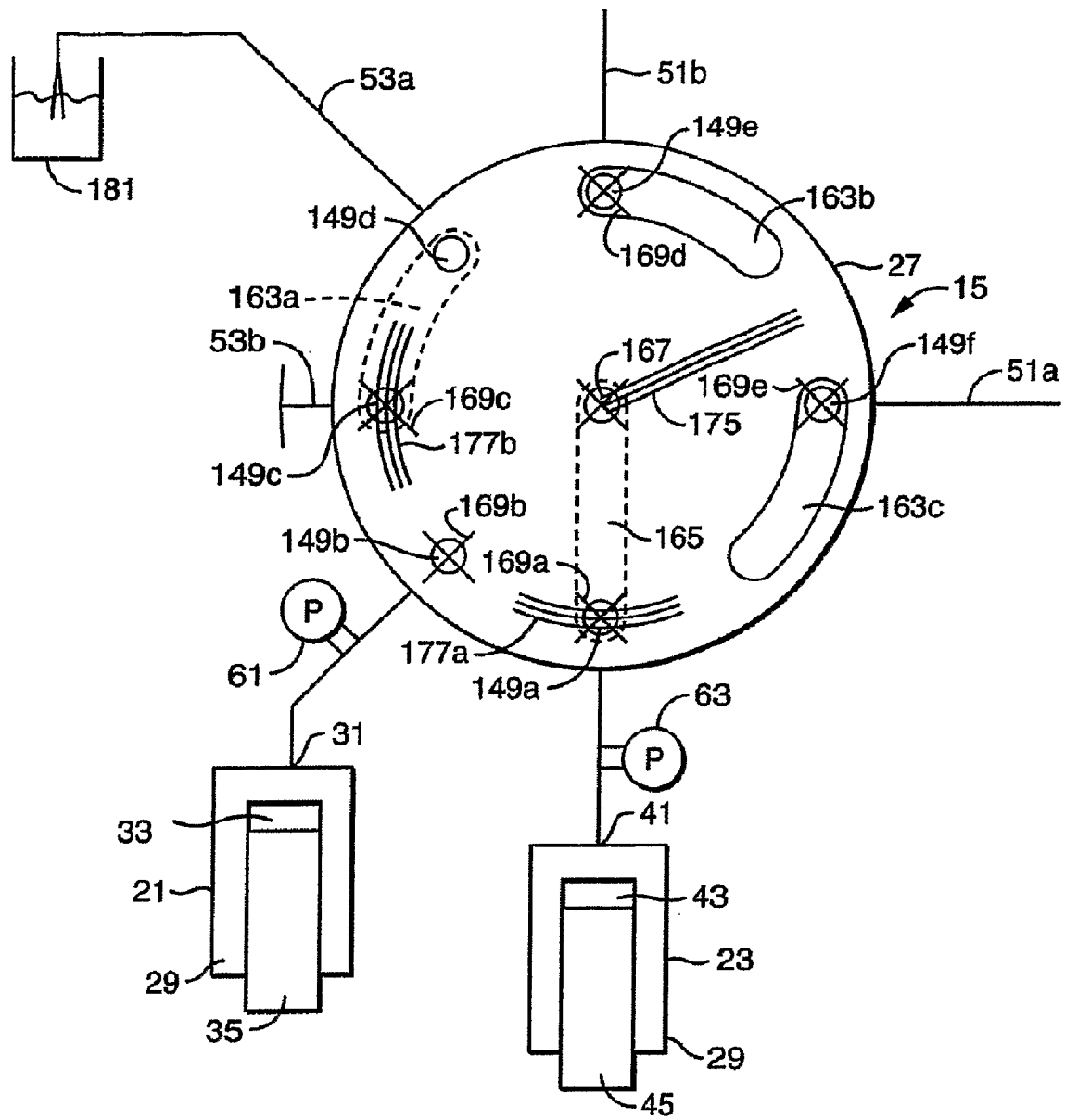
Figure 2E:
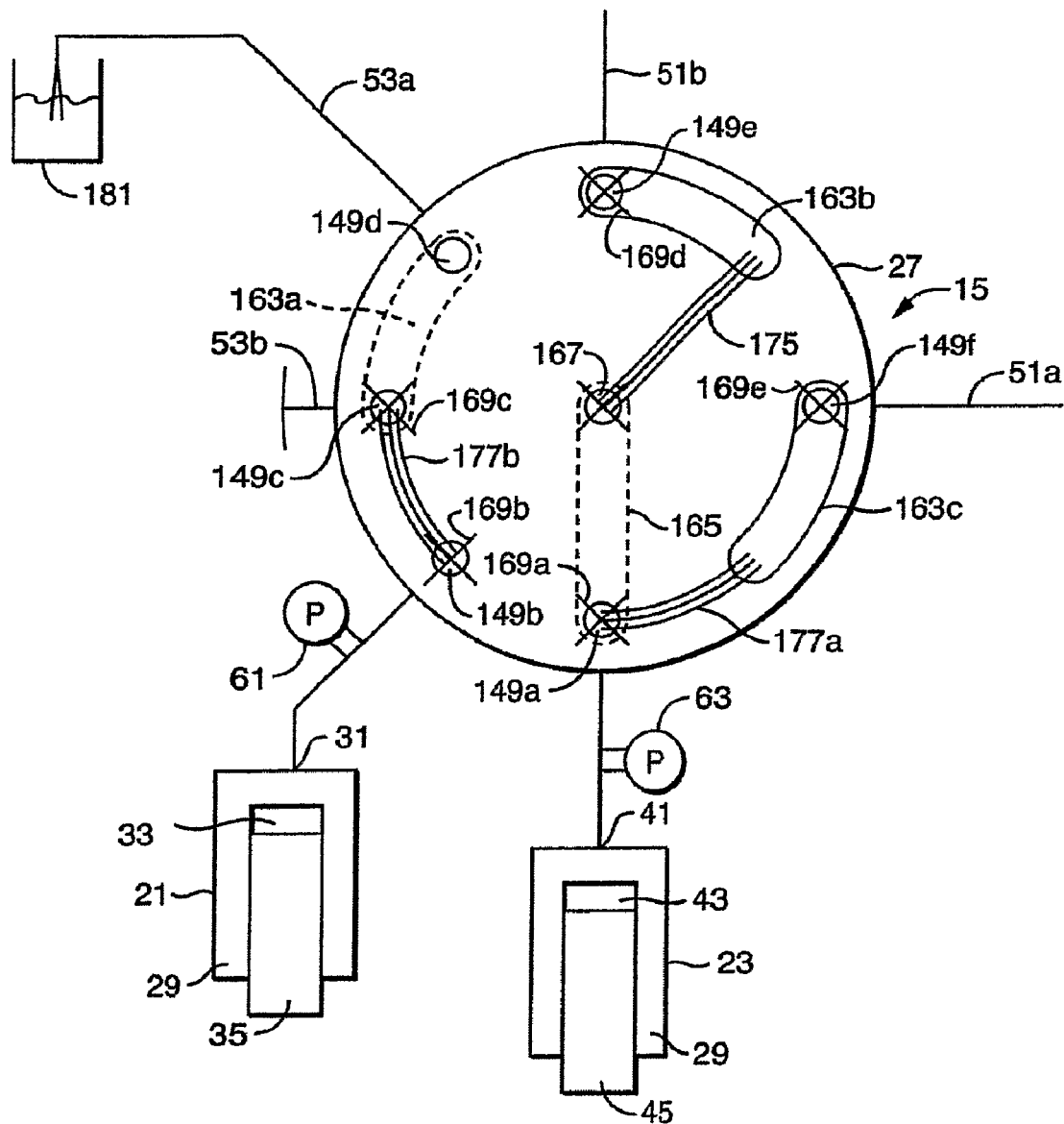
Figure 2F:
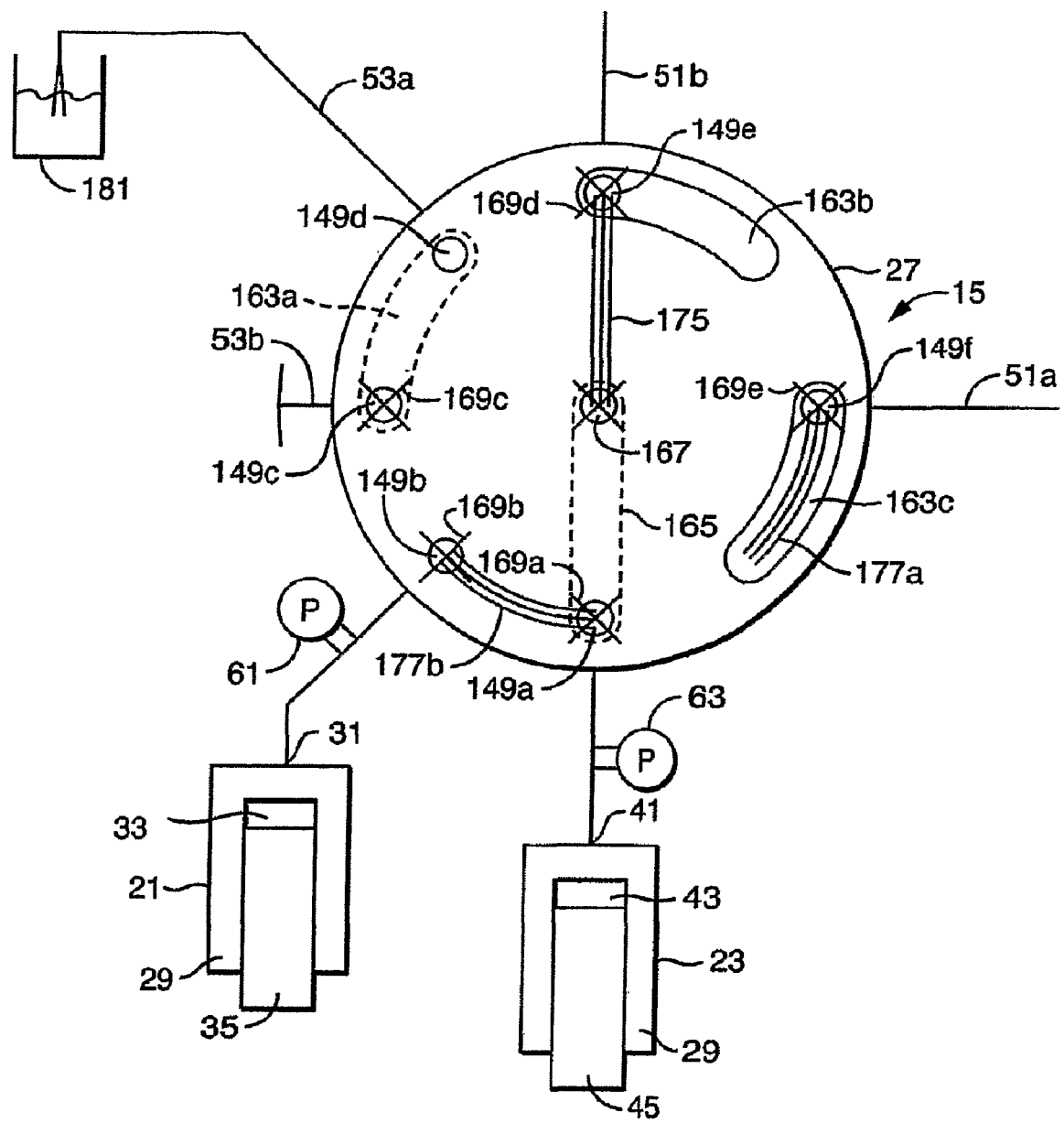

The radial rotor passage 175 is capable of selectable rotation to communicate with third arc channel 163c as best seen in FIG. 2A and third radial passage 163c and port 149f as best seen in FIGS. 2A, 2B and 2C; and second radial passage 163b and port 149e, as best seen in FIGS. 2E and 2F.

Returning now to FIGS. 2A and 3, the first rotor surface has a first arc channel 177a and a second arc channel 177b. The first arc channel 177a and the second arc channel 177b are arranged about a common radius defined by the rotation of the rotor 135 to bring one or more passages of the stator disc 141 in fluid communication. Thus, the first arc channel 177a and the second arc channel 177b are of a length that generally spans the distance between two adjacent through passages 169 a-f.

The rotor 135 is coupled to shaft 137 by pins 179a-c and cooperating holes 179 d-f in the rotor. Shaft 137 is coupled to a motor, solenoid, position sensors, mechanical linkages, gears and transmissions [not shown] for rotating the rotor 135 about an axis of rotation to a selected rotational position with respect to the stator disc 141. Motors, solenoids, position sensors, mechanical linkages and transmissions are known in the art. A preferred motor is a stepper motor that combines features of a position sensor and controlled movement. Stepper motors are available from several vendors such as identified previously.

Returning now to FIG. 2A, the first position depicted, in which ports 149a-f of the port plate are denoted with circles and through passages 169a-e are denoted with "x". Passages comprising channels or grooves between the stator disc 141 and the port plate 139 are denoted in dotted lines such as first arc passage 163 and first radial passage 165 of the stator disc 141. Passages comprising channels or groove in surfaces between the rotor 135 and the stator disc 141 are depicted in solid fines.

In the first position, the accumulator opening 41 and the first outlet 51a are in fluid communication via port 149a of the port plate 139, first radial passage 165 and center passage 167 of the stator disc 141, and radial rotor passage 175 of rotor 135, and third arc passage 163c exiting through passage 169f of the stator disc 141 and port 149f of the port plate 139.

In this first position, the primary opening 31 is in fluid communication with the first inlet 53a via port 149b through passage 169b of the stator disc 141, first arc passage 177b of the rotor 135, through passage 169c and first arc passage 163a of the stator disc 141, and port 149d of port plate 139. Second arc channel 177b of rotor 135 does not communicate with plate port 149d because there is no through passage at such port. And, first arc passage 163a of the stator disc 141 is between the stator disc 141 and the port plate 139.

To facilitate priming of the primary pump 21, the primary opening 31 is also in communication with port 149c of the port plate 139. Port 149c is in communication with a second inlet 53b used as an injection port [not shown]. Injection ports are known in the art and are commonly used to facilitate priming of pumps. A needle syringe [not shown] is received in second inlet 53b and fluid in withdrawn from the first inlet 53a, through port 149d of the port plate, first arc passage 163a and through passage 169c of the stator disc 141. The fluid is forced or propelled into the primary pump chamber 33 as the primary pump 21 is directed by control means 13, depicted in FIG. 1, to undergo a loading movement.

In this first position, in the event chamber 43 of the accumulator pump 23 was filled with fluid, directions from the control means 13, as depicted in FIG. 1, to undergo a pumping motion, forces fluid from port 149f and first outlet 51a.

Turning now to FIG. 2B, the rotor 135 has rotated towards the second position and is depicted in a first intermediate position, between the first position depicted in FIG. 2A, and the second position, depicted in FIG. 2C. In the first intermediate position, the accumulator chamber 41 is in communication with the first outlet 51a via port 149a of the port plate 139, first radial passage 165 and center passage 167 of the stator disc 141 and radial rotor passage 175. Through passage 169a of the stator disc 141 is blocked at the rotor 135. The primary opening 31 is closed at first arc passage 177a of the rotor 135. First arc passage 177a does not communicate with any further passageways.

The closed primary chamber 33 allows the primary drive means, depicted in FIG. 1, to power the primary piston 35 to bring the pressure of the primary chamber 33 to a pressure corresponding to the pressure of the accumulator chamber 43 as measured by the first pressure sensor 61 and the second pressure sensor 63. Matching the pressure of the accumulator chamber and the primary chamber minimizes pressure perturbations.

In addition, the intermediate position is preferably used to check for system failure. System failure can be performed by powering the primary pump 21 with the valve 27 in the intermediate position. The closed primary chamber 33 becomes pressurized and the values of the first pressure sensor 61 can be compared to anticipated control values, or the rate of decay of the pressure values compare to a control rate of decay. Failure to attain or maintain the pressure values or steeper decay rates are indicative of leaks.

Now moving to FIG. 2C, the rotor 135 has rotated to the second position. In the second position, the primary opening 31 of the primary pump 21 and the accumulator opening 41 of the accumulator pump are in fluid communication with the first outlet 51a and with each other. In greater detail, primary opening 31 is in fluid communication with port 149b of the port plate 139, and through passage 169b of the stator disc 141 and first arc passage 177a of rotor 135. First arc passage 177a of rotor 135 extends between through passage 169b and through passage 169a of the stator disc 141. And, through passage 169a is in fluid communication with port 149a of the port plate 139 and accumulator opening 41. Through passage 165a is also in fluid communication with first radial passage 165 and center passage 167 of the stator disc 141 and radial rotor passage 175 of the rotor 135. Radial rotor passage 175 is in fluid communication with third arc passage 163c and through passage 169e of the stator 141, and port 149f of the port housing 139.

In the second position, the control means 13, as best seen in FIG. 1, commands the accumulator pump 23 to undergo a loading movement and the primary pump 21 to undergo a pumping movement. Primary pump 21 maintains the flow of fluid through first outlet 51a and fills accumulator chamber 43.

In the normal operation of the pump 15, the valve 27 would move back and forth between the first position and the second position represented by FIGS. 2A and 2C, with the pressure of primary pump 21 matched with the pressure of accumulator pump 23 at a first intermediate position, as described with respect to FIG. 2B.

Turning now to FIG. 2D, a second intermediate position of valve 27 is depicted. In the second intermediate position, the accumulator opening 41 is closed. Accumulator opening 41 is in fluid communication with port 149a of the port plate 139, first radial passage 165 and center passage 167 of the stator disc 141 and radial rotor passage 175 of the rotor 135. However, the radial rotor passage 175 does not communicate with any further passage or port. The first arc passage 177a also does not communicate with any further passage or port.

The second intermediate position is used to check for system failure. System failure can be performed, preferably, under the direction of control means 13 depicted in FIG. 1, by powering the accumulator pump 23 with the valve 27 in the second intermediate position. The closed accumulator chamber 43 becomes pressurized and the values of the second pressure sensor 63 can be compared to anticipated control values, or the rate of decay of the pressure values compare to a control rate of decay. Failure to attain or maintain the pressure values or steeper decay rates are indicative of leaks.

In the second intermediate position, the primary opening 31 is also closed. Primary opening 31 is in fluid communication with port 149b of the port plate 139 and through passage 169b of the stator disc 141. However, through passage 169b of the stator disc 141 does not communicate further with any other inlet or outlet.

The control means 13, as described with respect to FIG. 1, directs the valve 27 to assume the second intermediate position and the accumulator pump 23 to assume a pump movement to check for system failure by comparing the pressure signal from the second pressure sensor 63 to predetermined minimum values and a values determined by a pressure value decay rate. Failure to attain or maintain anticipated pressure values or decay rates steeper than control values are indicative of leaks. The pressures of pressure sensor 61 and pressure sensor 63 reflecting the pressures of primary chamber 33 and accumulator chamber 63, respectively, can be compared to each other. Deviations between the pressures or decay rates in pressures in primary chamber 33 and accumulator chamber 43 are indicative of system failure.

Preferably, the control means 13 is programmed to automatically check for system failure. This can be performed with each pump cycle with respect to the primary pump 21 and at between methods, at start up or shut down with respect to the accumulator pump 23.

Turning now to FIG. 2E, the valve means 27 is depicted in a third position. This third position utilizes the second outlet 51b. In the third position, the accumulator opening 41 is in fluid communication with the second outlet 51b via port 149a of the port plate 139, first radial passage 165 and center passage 167 of the stator disc 141 and radial rotor passage 175 of the rotor 135, second arc passage 163b and fourth through passage 169d of stator 141, and port 149e of port plate 139. Second outlet 51b allows the accumulator pump 23 to discharge fluid, preferably, to waste to allow the accumulator pump 21 to vent.

In this third position, the primary outlet 31 is in fluid communication with the first inlet 53a, and if desired, the second inlet 53b for priming. Primary pump opening 31 is in fluid communication with port 149b of the port plate, second through passage 169b of the stator disc 141, second arc passage 177b of the rotor 135, port 149c of the port plate 139, first arc passage 163 of the stator disc 141 and port 149d of the port plate 139. Thus, primary pump 21 upon receiving commands for the control means 13, shown in FIG. 1, to assume a loading position, fills with fluid. Primary chamber 33 can be primed as with the first position previously described.

Turning now to FIG. 2F, the valve means 27 is depicted in a fourth position. In the fourth position, the accumulator opening 41 is in fluid communication with the second outlet 51b and the primary opening 31. In the fourth position, the primary opening is in fluid communication with port 149b of the port plate 139, second through passage 169b of the stator disc 141, second arc passage 177b of the rotor 135, first through passage 169a, first radial passage 165 center passage 167 of stator disc 141, radial rotor passage 175 of the rotor 135, fourth through passage 169e of stator disc 141 and port 149e of port plate 139. The accumulator opening 41 is in fluid communication with port 149 of the port plate 139, and shares first through passage 169a of the stator disc 141 and all subsequent passages as the primary opening 31. The control means 13, as depicted in FIG. 1, is capable of commanding the valve means 27 to assume the third position and said accumulator pump 23 and primary pump 21 to assume a pump position to empty the primary chamber 33 and accumulation chamber 43. Or, the control means 13 is capable of commanding the accumulator pump 23 to assume a load position as the primary pump 21 assumes a pump position to fill the accumulator chamber 43 and maintain flow at the second outlet 51b. The valve means 27 is capable of alternating between the third and fourth positions as the accumulator pump 23 and primary pump 21 alternate between pump mode and loading mode to pump fluid to waste through second outlet 51b.

Returning now to FIG. 1, the device 11 is depicted with a first pump assembly 15 and a second pump assembly 17. Tandem pump assembles are preferred in situations where the solutions being pumped need to change composition. The first pump assembly 15 is in fluid communication with a vessel 181 having a first fluid and the second pump assembly is in fluid communication with a second vessel 183 having a second fluid, or, if a second fluid is not desired, a single pump assembly 15 can be used or the pump assemblies 15 and 17 can be plumbed to the same vessel or vessels having the same fluid as known in the art.

As depicted, the first pump assembly 15 has a first outlet 51a in fluid communication with a combined outlet 59 and second pump assembly 17 has a first outlet 51b' in communication with the combined outlet 59 to allow fluid having different ratios of a first and second fluid to be formed. The control means 13 for the second pump assembly 17 is preferably shared with that of the first pump assembly 15. However, a second control means [not shown] for the second pump assembly can be readily employed and a third control means [not shown], to calculate the pumping rates of the first pump assembly 15 and the second pump assembly 17 to attain the desired ratios may also be employed.

The ratio of said first fluid and second fluid is changed by altering the rate of the pumping mode of at least one primary pump 31 or 31' or accumulator pump 23 and 23' of the first pump assembly 15 and second pump assembly 17.

A embodiment of the present invention is directed to a method for propelling fluids which also describes the operation of the device 11. The method comprising the step of providing at least one first pump assembly 15 having a primary pump 21, an accumulator pump 23, valve means 27, and control means 13. And, the method comprises the step of operating the one pump assembly 15 to propel fluids as control means 13 commands the valve means 27 to assume a first position and a second position and commands the primary pump 21 and accumulator pump 23 to alternate between a loading movement and a pump movement.

Thus, embodiments of the present invention are directed to pumps capable of pumping the liquids and gases used in chromatographic processes at a constant flow rate with minimal pressure perturbations. Embodiments featuring tandem pump assemblies are ideally suited to pump solutions changing in composition over time. The pump accomplishes these tasks with a minimum of moving mechanical parts in contact with fluids.

Thus, embodiments of the present invention have been described as to the best mode with the understanding that the features described are subject to modification and alteration and should not be limited to the precise details but should encompass the subject matter of the claims that follow and their equivalents.

What is claimed:

1. A device for propelling fluids comprising:
   a. at least one first pump assembly having a primary pump, an accumulator pump and valve means;
      i. said primary pump having a primary housing a primary piston and primary drive means, said primary housing having a primary opening and primary chamber, said primary opening in fluid communication with said primary chamber and said primary piston movable within said primary chamber to move fluids through said primary opening and said drive means mechanically linked to at least one of said primary piston and primary chamber to power said primary piston in a loading movement and a pump movement;
      ii. said accumulator pump having an accumulator housing, accumulator piston and accumulator drive means, said accumulator housing having an accumulator opening and accumulator chamber, said accumulator opening in fluid communication with said accumulator chamber and said accumulator piston movable within said accumulator chamber to move fluids through said accumulator opening, and said accumulator drive means mechanically linked to at least one of said accumulator piston and accumulator chamber to power said primary piston in a loading movement and a pump movement;
      iii. said valve means in fluid communication with said accumulator opening and said primary opening, and said valve means having a first outlet and a first inlet, and at least a first position and a second position, said inlet for receiving fluid and said outlet for discharging fluid, in said first position said accumulator opening and said first outlet are in fluid communication and said primary opening is in fluid communication with said first inlet, and upon said accumulator pump assuming said pump movement said first outlet discharging fluid and upon said primary opening assuming said loading movement said primary chamber filling with fluid; and in said second position said primary pump opening, accumulator pump opening and first outlet are in fluid communication and upon said primary pump assuming said pumping movement and said accumulator pump assuming said loading movement said accumulator chamber filling with fluid and said first outlet discharging fluid, said valve means moving between said first position and said second position as said accumulator pump and primary pump alternate between a loading movement and a pump movement; and
   b. control means, said control means in signal communication with said accumulator pump, said primary pump and said valve means, said control means commanding said accumulator pump to assume said loading movement and said pump movement and said primary pump to assume said loading movement and pump movement in coordination with said movement of said valve means such that fluids are propelled from the first outlet.

2. The device of claim 1 further comprising at least one first pressure sensor in fluid communication with said primary pump, said at least one first pressure sensor for producing at least one first pressure signal indicative of the pressure in said primary pump to allow control means to command said valve means to assume said second position.

3. The device of claim 2 further comprising at least one second pressure sensor in fluid communication with said accumulator pump, said at least one second pressure sensor for producing at least one second pressure signal indicative of the pressure of the pressure in said accumulator pump to allow the control means to command facilitate said valve means to assume said second position.

4. The device of claim 1 further comprising at least one first pressure sensor and at least in one second pressure sensor, said first pressure sensor in fluid communication with said primary pump, said at least one first pressure sensor for producing at least one first pressure signal indicative of the pressure in said primary pump, and said at least one second pressure sensor in fluid communication with accumulator pump, said at least one second pressure sensor for producing at least one second pressure signal indicative of the pressure in said accumulator pump, said control means commanding said valve means to assume said second position with said primary pump in fluid communication with said accumulator pump upon said first pressure signal corresponding to said second pressure signal.

5. The device of claim 4 wherein said control means commands said valve means to assume said first position upon said accumulator completing a loading movement with said accumulator assuming a pump movement and said primary assuming a loading movement.

6. The device of claim 5 wherein said valve means has a first intermediate position, in said first intermediate position in between said first position and said second position, and in said first intermediate position said accumulator chamber is in communication with said outlet and said primary chamber is closed.

7. The device of claim 6 wherein said control means directs said valve means to assume said first intermediate position and said primary pump to assume a pump movement said control means performing at least one of the functions selected from the group consisting of checking for system failure and bringing pressure in said primary chamber to a discharge pressure.

8. The device of claim 7 wherein said control means checks for system failure by comparing said pressure signal from said primary pressure sensor to at least one of the values selected from the group consisting of a predetermined minimum value and a value determined by a pressure value decay rate.

9. The device of claim 6 wherein said valve means has a second intermediate position, in said second intermediate position said accumulator opening is closed.

10. The device of claim 8 wherein said control means directs said valve means to assume said second intermediate position and said accumulator pump to assume a pump movement said control means checking for system failure.

11. The device of claim 9 wherein said control means checks for system failure by comparing said pressure signal from said accumulator pressure sensor to at least one of the values selected from the group consisting of a predetermined minimum value and a value determined by a pressure value decay rate.

12. The device of claim 1 wherein said valve means has a second outlet and a third position, in said third position said accumulator opening is in fluid communication with said second outlet and said primary opening is in fluid communication with said first inlet, said fourth position allowing said control means to commanding said valve means to assume said third position and said accumulator pump and primary pump to assume a pump position to empty said primary chamber and accumulation chamber.

13. The device of claim 12 wherein said second outlet is in communication with waste.

14. The device of claim 13 wherein said control means commands said valve means to assume said third position and said accumulator pump and primary pump to assume a pump mode to discharge fluid to waste.

15. The device of claim 13 wherein said valve means has a fourth position, in said fourth position said accumulator opening is in fluid communication with said second outlet to allow said accumulator pump to discharge fluid, and valve means to alternate between said third and fourth positions as said accumulator pump and primary pump alternate between pump mode and loading mode to pump fluid to waste.

16. The device of claim 1 further comprising a second pump assembly, said first pump assembly having valve means with said first inlet for being placed in fluid communication with a first fluid and said second pump assembly having a first inlet for being placed in fluid communication with a first fluid or a second fluid, said first pump assembly having a first outlet in fluid communication with a combined outlet and second pump assembly having a first outlet in communication with a combined outlet to allow fluid having different ratios of a first and second fluid to be formed.

17. The device of claim 16 wherein said control means changes the ratio of said first fluid and second fluid by changing the rate of the pumping mode of at least one primary or accumulator pump.

18. The device of claim 1 wherein said valve means has a second inlet, said second inlet capable of being placed in fluid communication with priming apparatus when said valve means is in said first position.

19. The device of claim 18 wherein said priming apparatus is selected from syringes pumps and pressurized fluid sources.

20. A valve for controlling a pump assembly having a primary pump, an accumulator pump;
  i. said primary pump having a primary housing, primary piston, said primary housing having a primary opening and primary chamber, said primary opening in fluid communication with said primary chamber and said primary piston movable within said primary chamber to move fluids through said primary opening and having a loading movement and a pump movement;
  ii. said accumulator pump having an accumulator housing, accumulator piston and accumulator drive means, said accumulator housing having an accumulator opening and an accumulator chamber, said accumulator opening in fluid communication with said accumulator chamber and said accumulator piston movable within said accumulator chamber to move fluids through said accumulator opening, and having a loading movement and a pump movement;
  said valve comprising:
  a valve housing, a rotor means, and positioning means,
  i. said valve housing having an accumulator port, a primary port, a first inlet port, a first outlet port, first stator surface, and a second surface, said accumulator port for placement in fluid communication with said accumulator opening and said primary port for placement in fluid communication with said primary opening, said first inlet port for placement in communication with said first inlet and said first outlet port for placement in communication with said first outlet, said first stator surface in sealing contact with a first rotor surface of said rotor means and having a first accumulator stator opening in fluid communication with said accumulator port, a first primary stator opening in fluid communication with said primary port, a first inlet stator opening in fluid communication to said first inlet port, and a first outlet stator opening in fluid communication with said first housing outlet port, ii. said rotor means comprising a body with a first rotor surface, a second rotor surface, an axis of rotation and rotor passage means, said first rotor surface in sealing contact with said first stator surface, said rotor passage means in selectable communication with said accumulator stator opening, said primary stator opening said inlet stator opening, and said outlet stator opening, said rotor means coupled to positioning means for rotation about an axis of rotation to assume a first position and a second position, in said first position said accumulator opening and said first outlet are in fluid communication and said primary opening is in fluid communication with said first inlet, and in said second position said primary pump opening, accumulator pump opening and first outlet are in fluid communication, iii. positioning means coupled to said rotor means to power said rotor means to one of said first position and second position to allow said valve to direct fluids in and out of said accumulator chamber and primary chamber in response to pumping and loading movements.

21. The device of claim 20 wherein said housing further comprises a stator body and a first housing surface, and said first stator surface is integral to said stator body, said stator body has a second stator surface, said second stator surface received in sealing relationship to said first housing surface and said first housing surface has an accumulator housing opening in fluid communication with said accumulator port, a primary housing opening in fluid communication with said primary port, a inlet housing opening in fluid communication to said first inlet port, and a outlet housing opening in fluid communication with said first housing outlet port, and said stator second surface has a second accumulator stator opening in fluid communication with said first accumulator stator opening, a second primary stator opening in fluid communication with said first primary stator opening, a second inlet stator opening in fluid communication with said first inlet stator opening, and a second outlet stator opening in fluid communication with said first stator outlet.

22. The device of claim 21 wherein said stator body said first accumulator stator opening, said first primary stator opening, said first inlet stator opening, and said first stator outlet arranged about a common radius defined by the rotation of said rotor means.

23. The device of claim 22 wherein said first accumulator opening has a radial channel section extending from said common radius to said axis of rotation on the first stator surface.

24. The device of claim 23 wherein said rotor means has a first rotor channel extending from said common radius to said axis of rotation on said first rotor surface to cooperate with said radial channel section.

25. The device of claim 21 wherein said rotor has a second rotor passage on said first rotor surface, said second rotor passage extending axially about said common axis to bring said first accumulator stator opening in fluid communication with said first primary stator opening in said first position.

26. The device of claim 21 wherein said valve housing has a second outlet and a rotor has a third rotor channel on said first rotor surface, said third rotor passage extending axially about said common axis to bring said first accumulator stator opening in fluid communication with said first primary opening as said rotor is in fluid communication with said second outlet to allow said primary pump and accumulator pump assume a loading and pumping movement as with respect to said second outlet.

27. The device of claim 26 wherein said stator body has a second stator outlet in fluid communication with said second outlet and said second stator outlet has a third stator channel extending axially about said common axis a distance permitting said rotor to maintain fluid communication as said primary pump and accumulator pump assume a loading and pumping movement.

28. The device of claim 21 wherein said housing has a second inlet and said stator body has a second stator inlet opening in fluid communication with said second inlet, said second stator inlet opening having a passage to said first inlet opening to allow said second inlet to receive priming fluids.

29. A method for propelling fluids comprising the steps of:
a providing at least one first pump assembly having a primary pump, an accumulator pump and valve means;
i. said primary pump having a primary opening, primary chamber and an a primary piston, said primary opening in fluid communication with said primary chamber and said primary piston movable within said primary chamber to move fluids through said primary opening and having a loading movement and a pump movement;
ii. said accumulator pump having a accumulator opening, accumulator chamber and an accumulator piston, said accumulator opening in fluid communication with said accumulator chamber and said accumulator piston movable within said accumulator chamber to move fluids through said accumulator opening, and having a loading movement and a pump movement;
iii. said valve means in fluid communication with said accumulator opening and said primary opening, and said valve means having a first outlet and a first inlet, and at least a first position and a second position, said inlet for receiving fluid and said outlet for discharging fluid, in said first position said accumulator opening and said first outlet are in fluid communication and said primary opening is in fluid communication with said first inlet, and upon said accumulator pump assuming said pump movement said first outlet discharging fluid and upon said primary opening assuming said loading movement said primary chamber filling with fluid; and in said second position said primary pump opening, accumulator pump opening and first outlet are in fluid communication and upon said primary pump assuming said pumping movement and said accumulator pump assuming said loading movement said accumulator chamber filling with fluid and said first outlet discharging fluid, said valve means moving between said first position and said second position as said accumulator pump and primary pump alternate between a loading movement and a pump movement;
providing control means, said control means in signal communication with said accumulator pump, said primary pump and said valve means, said control means commanding said accumulator pump to assume said loading movement and said pump movement and said primary pump to assume said loading movement and pump movement in coordination with said movement of said valve means such that fluids are propelled from the first outlet; and
c. operating said at least one pump assembly to propel fluids as control means commands said valve means to assume a first position and a second position and commands said primary pump and accumulator pump to alternate between a loading movement and a pump movement.

* * * * *